United States Patent
Gizurarson et al.

(10) Patent No.: US 9,968,648 B2
(45) Date of Patent: May 15, 2018

(54) PEPTIDE OR PROTEIN STABILIZING FORMULATION

(71) Applicant: Calor ehf, Reykjavik (IS)

(72) Inventors: Sveinbjorn Gizurarson, Reykjavik (IS); Stefan Jon Sigurdsson, Reykjavik (IS)

(73) Assignee: Calor ehf., Reykjavik (IS)

( * ) Notice: Subject to any disclaimer, the term of this patent is extended or adjusted under 35 U.S.C. 154(b) by 0 days. days.

(21) Appl. No.: 15/310,287

(22) PCT Filed: May 15, 2015

(86) PCT No.: PCT/IS2015/050009
§ 371 (c)(1),
(2) Date: Nov. 10, 2016

(87) PCT Pub. No.: WO2015/173839
PCT Pub. Date: Nov. 19, 2015

(65) Prior Publication Data
US 2017/0157201 A1 Jun. 8, 2017

(30) Foreign Application Priority Data
May 14, 2014 (IS) .......................... 050080

(51) Int. Cl.
| | |
|---|---|
| *A61K 47/10* | (2017.01) |
| *A61K 47/26* | (2006.01) |
| *A61K 38/11* | (2006.01) |
| *A61K 9/08* | (2006.01) |
| *A61K 47/02* | (2006.01) |

(52) U.S. Cl.
CPC ............ *A61K 38/11* (2013.01); *A61K 9/08* (2013.01); *A61K 47/02* (2013.01); *A61K 47/10* (2013.01); *A61K 47/26* (2013.01)

(58) Field of Classification Search
CPC ............ A61K 38/08; A61K 38/1709; A61K 39/39591; A61K 47/10; A61K 47/26; C07K 7/16; C07K 14/4715; C12N 9/96
See application file for complete search history.

(56) References Cited

U.S. PATENT DOCUMENTS

| | | | | |
|---|---|---|---|---|
| 4,153,689 A | * | 5/1979 | Hirai ................ | A61K 9/0043 514/5.9 |
| 2006/0088592 A1 | | 4/2006 | Choi et al. | |
| 2008/0286280 A1 | * | 11/2008 | Kallmeyer ......... | A61K 9/0019 424/141.1 |
| 2013/0101584 A1 | | 4/2013 | Manning et al. | |
| 2013/0189322 A1 | * | 7/2013 | Honeyman ........ | A61K 47/48776 424/400 |
| 2017/0224820 A1 | * | 8/2017 | Ji .................... | A61K 39/39591 |

FOREIGN PATENT DOCUMENTS

| | | |
|---|---|---|
| EP | 1902705 A1 | 3/2008 |
| EP | 1908482 A1 | 4/2008 |
| EP | 2161030 A1 | 3/2010 |
| WO | WO-2004/078147 A2 | 9/2004 |
| WO | WO-2011/119487 A2 | 9/2011 |

OTHER PUBLICATIONS

Arakawa et al., "Protein—solvent interactions in pharmaceutical formulations," Pharm Res. 8(3):285-91 (1991).
Avanti et al., "A new strategy to stabilize oxytocin in aqueous solutions: I. The effects of divalent metal ions and citrate buffer," AAPS J. 13(2):284-90 (2011).
Bhat et al., "Steric exclusion is the principal source of the preferential hydration of proteins in the presence of polyethylene glycols," Protein Sci. 1(9):1133-43 (1992).
Hammes et al., "An investigation of water-urea and water-urea-polyethylene glycol interactions," J Am Chem Soc. 89(2):442-6 (1967).
Hawe et al., "Towards heat-stable oxytocin formulations: analysis of degradation kinetics and identification of degradation products," Pharm Res. 26(7):1679-88 (2009).
Hinz et al., "Fundamentals of protein stability," Pure & Appl Chem. 65(5):947-52 (1993).
Izutsu et al., "Stabilizing effect of amphiphilic excipients on the freeze-thawing and freeze-drying of lactate dehydrogenase," Biotechnol Bioeng. 43(11):1102-7 (1994).
Jacob et al., "Stability of proteins in aqueous solution and solid state," Indian J Pharm Sci. 68(2):154-63 (2006).
Khan et al., "Effect of sugars on rabbit serum albumin stability and induction of secondary structure," Biochemistry (Mosc). 66(9):1042-6 (2001).
Lee et al., "Thermal stability of proteins in the presence of poly-(ethylene glycols)," Biochemistry. 26(24):7813-9 (1987).
Sigurdsson, Stefán Jón, Thesis Abstract: "Effects of different sugars and polyethylene glycol polymers on the thermal stability of oxytocin in aquous solution," submitted Apr. 2014 <http://skemman.is/en/browse/author/Stefán+Jón+Sigurðsson+1985> (2 pages).
Sola-Penna et al., "Stabilization against thermal inactivation promoted by sugars on enzyme structure and function: why is trehalose more effective than other sugars?" Arch Biochem Biophys. 360(1):10-4 (1998).
Timasheff, "The control of protein stability and association by weak interactions with water: how do solvents affect these processes?" Annu Rev Biophys Biomol Struct. 22:67-97 (1993).

* cited by examiner

*Primary Examiner* — Jeffrey E. Russel
(74) *Attorney, Agent, or Firm* — Clark & Elbing LLP; Susan M. Michaud

(57) ABSTRACT

The invention relates to the use of a mixture of tetraethyleneglycol and amino sugars such as glucosamine or galactosamine to protect peptides and proteins and enhance their stability in solution.

20 Claims, No Drawings

PEPTIDE OR PROTEIN STABILIZING FORMULATION

FIELD OF INVENTION

The present invention is within the field of pharmaceutical formulations and protein and peptide stabilization, and in particular in the field of biopharmaceutical formulations.

INTRODUCTION

Peptide and protein stability is very dependent on the amino acid composition and sequence. It is well known that lyophilized peptides and proteins are generally more stable, than when they are dissolved in e.g. aqueous solution. Common degradation pathways for peptides and proteins include the following:

Hydrolysis—A common problem for peptides and proteins in a solution or in contact with humidity, especially for peptides containing exposed Aspartic acid residues (Asp; D) in the sequence.

Deamidation—This type of degradation usually results in inactivation of the peptide or the protein.

Oxidation—Under certain storage conditions, peptides and proteins may undergo oxidation. The pH of the solution is critical and may catalyze this reaction.

Diketopiperazine and pyroglutamic acid formation—This formation usually occurs when Glycine is in the third position from the N-terminus.

Racemization—If this occurs, there is a general loss of chiral integrity of the amino acid or the peptide or protein.

According to general guidelines in the field, to prevent or to minimize degradation it is recommended that isolated peptides and proteins are stored as dry powder (in a lyophilized form) at –20° C. or preferably at –80° C. Storing peptides and proteins in a solution frequently carries a risk of degradation and significantly reduced shelf life. New and improved means to stabilize protein solutions such as for biopharmaceutical formulations would be much appreciated in the art.

SUMMARY OF INVENTION

The present inventors have developed certain new formulations and method for keeping proteins and peptides stable in solutions, that show surprising stabilizing effects when compared to existing prior art alternatives. Embodiments of the invention using the oxytocin peptide as a model compound show very little degradation even after 32 days storage at 40° C. The new formulations are in some embodiments based on combinations of tetraethyleneglycol and amino sugars.

In one aspect, the invention provides an aqueous pharmaceutical formulation comprising a peptide or protein, at least one amino-containing sugar molecule, a polyethyleneglycol such as tetraethyleneglycol, and water or an isotonic aqueous solution.

In another aspect, the invention provides an aqueous pharmaceutical formulation comprising a peptide or protein, a polyethyleneglycol such as tetraethyleneglycol, and water or an isotonic aqueous solution.

In a further aspect, a method is provided for stabilizing a protein or peptide by dissolving and/or maintaining the protein or peptide in a solution comprising the above mentioned components.

Exemplary embodiments and advantages of the invention are described in the following.

DESCRIPTION OF THE INVENTION

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The stability of peptides and proteins is generally limited to a storage in a refrigerator (4° C.), freezer (–20° C.) or preferably in an ultrafreezer (–80° C.). The present inventors showed that certain molecules having amino-group attached are able to surprisingly efficiently increase the aqueous stability of peptides and proteins. Extensive studies on molecules having an amino-group, showed that such molecule must be within a very narrow and finely adjusted window, using e.g. glucosamine as a stabilizator. Additional work, combining polyethyleneglycol and derivatives with amino-containing molecules such as glucosamine did not result in significant improvement. However, when tetraethyleneglycol, a single component that may be found in the polyethylene glycol 200, 300 and 400, was mixed with amino-containing molecule such as glucosamine, the results were surprising.

Tetraethyleneglycol, which is a specific type of polyethyleneglycol containing four ethylene units, has the chemical structure shown in formula I, and the chemical formula $C_8O_5H_{18}$, written as linear formula $HO(CH_2CH_2O)_3CH_2CH_2OH$.

Formula (I)

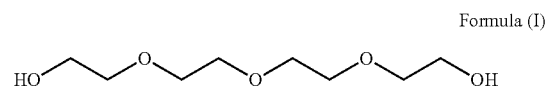 [SMILES: OCCOCCOCCOCCO]

Experiments by inventors further showed that solutions with TEG, with or without amino sugars, showed surprisingly stabilizing effect when stored for weeks a 40° C., and also after autoclaving after such storage. This is particularly useful for solutions intended for IV administration.

In one aspect of the invention, there is provided a pharmaceutical composition to increase aqueous stability of peptides or proteins, comprising: i) a peptide and/or a protein of interest; ii) a polyethyleneglycol, characterized by the presence of less than fourteen ethylene units; iii) water or isotonic aqueous solution; and iv) optionally, a physiologically acceptable vehicle.

In certain embodiments, the polyethyleneglycol can be selected from triethyleneglycol, tetraethylene glycol, pentaethyleneglycol, hexaethyleneglycol, and heptaethyleneglycol or mixtures of polyethyleneglycol such as PEG200, PEG300 or PEG400. In one preferred embodiment, the polyethyleneglycol is tetraethyleneglycol. In some embodiments, the polyethyleneglycol comprises a mixture of polyethyleneglycols that contain from 2-20 ethylene units, from 3-18 ethylene units, from 4-14 ethylene units, from 4-12 ethylene units, from 4-10 ethylene units, or from 4-8 ethylene units.

Another aspect of the invention relates to a pharmaceutical composition to increase aqueous stability of peptides or proteins, comprising: i) at least one peptide and/or a protein of interest; ii) at least one amino-containing sugar molecule; ii) a polyethyleneglycol, characterized by the presence of less than fourteen ethylene units; iii) water or isotonic aqueous solution; and iv) optionally, a physiologically acceptable vehicle.

Another aspect of the invention relates to a pharmaceutical composition to increase aqueous stability of peptides or proteins, comprising: i) a peptide and/or a protein of interest; ii) tetraethyleneglycol; iii) water or isotonic aqueous solution; and iv) optionally, a physiologically acceptable vehicle.

In some embodiments, the tetraethyleneglycol is substantially pure, i.e. free of other ethylene glycols. The tetraethylene glycol can also be provided as a mixture, for example as a mixture comprising tetraethylene glycol and at least one other polyethylene glycol. The additional polyethylene glycol can for example be triethyleneglycol, pentaethyleneglycol, hexaethyleneglycol, and so on. The tetraethyleneglycol can also be provided in a mixture with longer forms of polyethylene glycol. In such mixtures, the amount of tetraethylene glycol in the mixture can range from 40% to 99.9%, such as from 60% to 99.9%, 70% to 99.9%, 80% to 99.9%, 90% to 99.9%, 95% to 99.9%, 98% to 99.9%, 99.0% to 99.9% or 99.5% to 99.9%.

Another aspect relates to a pharmaceutical composition to increase aqueous stability of peptides or proteins, comprising: i) a peptide and/or a protein of interest; ii) at least one amino-containing sugar molecule; ii) a polyethyleneglycol, characterized by the presence of less than ten ethylene units; iii) water or isotonic aqueous solution; and iv) optionally, a physiologically acceptable vehicle. In certain embodiments, the polyethyleneglycol is selected from triethyleneglycol, tetraethylene glycol, pentaethyleneglycol, hexaethyleneglycol, and heptaethyleneglycol. In one preferred embodiment, the polyethyleneglycol is tetraethyleneglycol.

The amino-containing sugar molecule can be any amino-substituted sugar molecule, or a mixture of such molecules. The amino-substituted sugar molecule (i.e., aminosugar) can be substituted with one or multiple amino groups. The amino substitution is preferably at an hydroxyl group of the sugar molecule. The sugar molecule can be selected from any naturally occurring sugar. The sugar molecule can also be a non-naturally occurring sugar molecule. The sugar molecule can be a monosaccharide, or it can be a polysaccharide. In some embodiments, the sugar molecule is an amino-substituted monosaccharide.

The amino-containing sugar can also contain one or more further substitutions. The amino-containing sugar can for example be acetylated at the amino group.

In some embodiments, the sugar molecule is selected from glucosamine, galactosamine, fructosamine, mannitosamine, sialic acid, daunosamine. The sugar molecule can also be any acetyl-derivative thereof, such as for example N-acetylglucosamine.

This invention also relates to the use of amino-containing compounds such as in particular amino sugars and amino containing carbohydrates, such as but not limited to glucosamine, galactosamine, fructosamine, mannitosamine, N-acetylglucosamine, etc. together with tetraethyleneglycol in an aqueous solution or an isotonic aqueous solution to obtain an aqueous formulation for incorporating a protein or peptide. Thus, the pharmaceutical composition can in certain embodiments be a solution that comprises at least one protein or peptide, an amino containing carbohydrate such as an aminosugar, and tetraethyleneglycol.

The term isotonic solution refers in this context to a solution being isotonic with respect to normal human blood, creating no net osmotic pressure when administered in the blood stream.

The solutions of the invention are useful for preparing various solutions such as liquid biopharmaceutical solutions, such as in particular but not limited to solutions with active protein or peptide substance to be delivered, e.g. through IV, nasal spray or the like, where the substance is administered in liquid formulation.

It is advantageous that such solutions be provided to medical personnel in ready-to-use formulations for administration. It follows that for such solutions, in particular IV solutions, any excipients and additives used must fulfil strict criteria, such as for liquid to be delivered directly into the blood stream.

The amino sugar is preferably in a concentration in the range from about 0.001 M to about 1 M, such as in the range from about 0.01M to about 0.5M, and more preferably in the range from about 0.05M to about 0.4M, or in the range from about 0.05M to about 0.2M, such as but not limited to about 0.05 M, about 0.075 M, 0.1 M, or 0.15 M.

The polyethyleneglycol, for example tetraethyleneglycol, is preferably present in a concentration in the range from about 0.1% (vol/vol) to about 6%, such as in the range 025% to about 6%, or in the range from about 0.5% to about 6%, such as in the range of about 0.75% to about 2.5%, such as in the range 1% to about 2.5%, including but not limited to about 0.8%, 1.0%, 1.2%, 1.3%, 1.5%, 1.8%, 2.0%, 3.0%, 4.0%, 5.0%, and 6.0%.

The organic compounds (TEG and/or amino containing carbohydrate, such as amino sugars) may, as mentioned above, be mixed together with the peptide or protein of interest in water or aqueous solution, such as solutions of suitable salt and/or buffers. In some embodiment an isotonic aqueous solution is used, preferably comprising substances such as but not limited to sodium chloride, phosphate, potassium chloride or other pharmaceutically acceptable isotonic agents.

The present invention is applicable for a range of proteins and peptides such as but not limited to blood factors including factor II, factor VIII, factor IX, factor XIII, factor X; tissue plasminogen activator (tPA), peptide hormones such as but not limited to insulin, glucagon, adrenocorticotropic hormone (ACTH), growth hormone, vasopressin, oxytocin, cholecystokinin, gastrin, leptin, atrial-natriuretic peptide (ANP), atrial natriuretic factor (ANF); homeobox polypeptides, antibodies including monoclonal antibodies, secreted antibodies, antibody single chains including light chains and heavy chains, interferon including interferon-alfa, interferon-beta, interferon-gamma; interleukin, mannose-binding lectin, pepsin, chymotrypsin, trypsin, casein, human growth hormone, human serum albumin, human insulin, cellulases, pectinases, hemicellulases, phytases, hydrolases, peroxidases, fibrinogen, thrombin, protein C, xylanase, isoamylase, glucoamylase, amylases, lysozyme, beta-glucanase, glucocerebrosidase, caseins, lactase, urease, glucose isomerase, invertase, streptavidin, esterases, alkaline phosphatase, protease inhibitors, pepsin, chymotrypsin, trypsin, papain, kinases, phosphatases, deoxyribonucleases, ribonucleases, phosphlipases, lipases, laccase, spider silk proteins, antifreeze proteins, antimicrobial peptides or defensins, growth factors and cytokinins.

The invention is particularly useful for preparing pharmaceutical compositions in the form of solutions such as solutions suitable for administration via injection such as but not limited to intravenous, intramuscular, subcutaneous, intrathecal, intraosseus delivery, as a solution for storing peptides and proteins in the body such as but not limited to osmotic pumps and implants, for topical delivery such as but not limited to the skin and the ear and for mucosal delivery such as but not limited to the eye, the nose, the lungs, the vagina, the uterus, the urethra, the GI tract, the rectum the buccal and the sublingual mucosae.

TEG may be found in certain PEG products (such as PEG 200); in some embodiments the TEG is substantially free from other PEG compounds. Accordingly, in certain embodiments, the composition of the invention comprises less than about 1.0% (vol/vol) PEG compounds other than TEG, and more preferably less than about 0.5% such as less than 0.1%, and yet more preferably less than about 0.05% or less than about 0.01%.

The compositions of the invention can accommodate proteins and peptides at various concentrations, the desired concentration may depend on the intended use, and the particular protein or peptide. In some embodiments the protein of peptide is in a concentration in the range from about 0.01 µg/mL to about 150 mg/mL. For certain applications such as biopharmaceuticals with monoclonal antibodies, highly concentrated solutions have become increasingly popular. Products such as canakinumab (ILARIS®), efalizumab (RAPTIVA®), omalizumab (XOLAIR®), ustekinumab (STELARA®), adalimumumab (HUMIRA®), are provide either as lyophilized formulations to be reconstituted, or as highly concentrated solutions, up to 100 mg/mL concentration of the antibody.

For such and other biopharmaceutical products the present invention is very useful. Accordingly, in some embodiments the active protein or peptide is present in a concentration in the range from about 1 mg/mL to about 150 mg/mL, such as in the range from about 1 mg/mL to about 100 mg/mL, such as in the range from about 1 mg/mL to about 50 mg/mL, such as in the range from about 1 mg/mL to about 20 mg/m L, or in the range from about 10 mg/mL to about 50 mg/mL, or in the range from about 1 mg/mL to about 10 mg/m L.

In other embodiments with other protein or peptide agents, a low concentration of the protein or peptide is desired, such as but not limited to in the range from about 0.01 µg/mL to about 1 mg/mL, such as in the range from about 0.01 µg/mL to about 100 µg/mL, such as in the range from about 0.01 µg/mL to about 10 µg/mL, such as in the range from about 0.01 µg/mL to about 1 µg/mL, or in the range from about 0.1 µg/mL to about 1 µg/mL.

It follows that the volume is not critical, such as of a dose vial of a formulation of the invention, any desired volume can be prepared and administered according to the invention and the protein or peptide drug may be administered in a composition of the invention in a pharmaceutically acceptable amount to the site where it must be administered.

In an aspect, the invention also provides a method for stabilizing at least one protein or peptide in solution comprising mixing together at least one protein or peptide, a polyethelyneglycol that has fourteen or fewer ethylene units, and which is preferably in a concentration from about 0.1 to about 10.0% (v/v), at least one amino sugar; and water or an aqueous solution. In some embodiments, the polyethyleneglycol is tetratethyleneglycol. In general the polyethyleneglycol is in concentration as described in the above. In some embodiments, the tetraethyleneglycol is in a concentration from about 0.1 to about 10.0% (v/v). The at least one amino sugar can preferably be selected from glucosamine, galactosamine, fructosamine, mannitosamine, and N-acetylglucosamine. The at least one amino sugar can further be present in a concentration from about 0.001M to about 1.0 M.

Particular embodiments of the invention relate to a pharmaceutical composition comprising:
  i. In the range from about 0.001 to about 1 M amino-containing sugar molecule such as but not limited to glucosamine, galactosamine, fructosamine, mannitosamine, N-acetylglucosamine etc., where the concentration should preferably be in the range from about 0.01 to about 0.6 M and more preferably in the range from about 0.05 to about 0.4 M concentration, depending on the particular protein or peptide and intended application.
  ii. In the range from about 0.1 to about 10.0% of a polyethyelenegycol that has less than fourteen ethylene units, where the concentration should preferably be in the range from 0.5 to about 10% and more preferably from 0.9 to 7% concentration. In a preferred embodiment, the polyethyleneglycol is tetraethyleneglycol.
  iii. Water or aqueous solution and preferably an isotonic aqueous solution using compounds such as, but not limited to sodium chloride, phosphate, potassium chloride or other pharmaceutically acceptable isotonic agents.
  iv. A therapeutically, prophylactically and/or diagnostically active peptide or protein.
  v. And optionally, a physiologically or pharmaceutically acceptable vehicle.

In this invention, a biologically active agent, which is a protein or peptide, is mixed together with the pharmaceutical composition according to this present invention, and this formulation can be used to elicit the stability of peptides and proteins as well as to increase the absorption of peptide and proteins drugs to any mammalian host or more specifically a human. Examples of biologically active peptides and proteins for which the present invention is particularly useful are hormones such as but not limited to calcitonin, vasopressin, desmopressin, oxytocin, insulin, glucagon, placental protein 13, galectins, growth hormones, monoclonal and polyclonal antibodies, peptides and proteins for fertility treatment such as choriogonadotropin, menotropin, follitropin alpha, follitropin beta and lutropin alpha. Other biologically active agents include but are not limited to peptides and proteins having antiviral, antiprion, antibacterial, antineoplastic, antiparasitic, anti-inflammatory and/or antifungal activity. They may act as neurotransmitter, neuromodulators, hormone, hormone releasing factor, hormone receptor agonist or antagonist. The peptide or protein may also be an activator or inhibitor of a specific enzyme, an antioxidant, a free radical scavenger or a metal chelating agent. The peptide or protein may further be any substance which is capable of acting as a stimulant, sedative, hypnotic, analgesic, anticonvulsant, antiemetic, anxiolytic, antidepressant, tranquillizer, cognition enhancer, agents preventing or healing amnesia, metabolic stimulator or inhibitor, appetite stimulator or inhibitor and/or narcotic antagonist or agonist.

The peptide or the protein may furthermore be any bioactive material found to be deficient in conjunction with the disorder being treated or prevented, for example, nutrients or metabolic precursors for producing neurotransmitters for the treatment of Alzheimer's disease or insulin for the treatment of obesity and diabetes. The agent may also be an antibody for the treatment of viral, bacterial, prion, parasitic infections or tumours and/or cancer or for diagnosis of diseases or disorders where polyclonal or monoclonal antibodies and/or/with biochemical markers characteristic of the diseases or disorder are used. Such diagnostic antibodies may be labelled with any labelling agent who may be suitable according to the invention. The peptide or the protein may also comprise of substances selected from the group consisting of adrenal hormones, amino acids, anorectics, antibiotics, anti-allergic agents, antibodies, anti-cholinergic agents, anti-depressants, anti-epileptica and anti-spasmolytica, anti-histaminic agents, anti-hypertensive agents, anti-inflammatory agents, anti-neoplastic agents, antiseptics, anti-tumor, anti-tussive expectorant (asthmatic agents), anti-viral and anti-cancer agents, beta-adrenergic blocking agents, blood factors such as factor VII, factor VIII etc, metabolism controlling agents, bone-metabolism controlling agents, bronchodilators, cardiotonics, cardiovascular regulatory hormones, chemoterapeutic agents, CNS-stimulants, diagnostics, dopaminergic agents, enzymes, gastrointestinal hormones, hypothalamus hormones and derivatives, hypotensives, local anesthetics, migraine treatment substances, narcotics, antagonists and analgetics, pancreatic hormones and derivatives, parasympathomimetics, parasympatholytics, Parkinson's disease substances, pituitary gland hormones and derivatives, pregnancy associated proteins or peptides, protease inhibitors, sedatives, sex-hormones, sympathomimetics, thyroid gland hormones and derivatives, tranquillizers, vasoconstrictors and vasodilators.

The stability promoting effect according to this invention can be readily confirmed and monitored with methods known in the art, such as HPLC, LC-MS, LC-MS-MS, GC, GC-MS, spectroscopy and/or ELISA assays. As used herein, "stability promoting effect and stability enhancing effect" is intended to mean the ability to increase and/or maintain the stability of a peptide or a protein.

Comparison of stability in the presence and absence of the stability-promoting agents can be performed by routine methods, such as comparisons by HPLC, LC-MS, LC-MS-MS, GC, GC-MS, spectroscopy or ELISA assays, and appropriate controls.

The enhanced stability can be a result of a direct protective effect on the peptide or the protein or due to a more advantageous and complex interaction between the stability promoting agents according the invention and the peptide or the protein.

The peptide or protein formulation according to the invention can be configured to be optionally administered in a pharmaceutically or physiologically acceptable vehicle, such as physiological or phosphate buffered saline, water, dextrose, ethanol polyols (such as glycerol or propylene glycol), and combinations thereof.

The formulation according to the invention can in some embodiments be in admixture with a dispersing or wetting agent, suspending agent, and/or one or more preservatives. Suitable dispersing or wetting agents are, for example, naturally occurring phosphatides, e.g., lecithin, or soybean lecithin; condensation products of ethylene oxide with e.g., a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate etc. Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g., Avicel RC 591), methylcellulose; alginates such as, e.g., sodium alginate, etc. Suitable examples of preservatives for use in formulations according to the invention are parabens, such as methyl or propyl p-hydroxybenzoate, and benzalkonium chloride.

Pharmaceutically acceptable excipients may include, antioxidants, buffering agents, preservatives, humectants and perfumes. Examples of antioxidants are ascorbic acid and derivatives thereof, tocopherol and derivatives thereof, butylated hydroxy anisole (BHA), and cysteine. Examples of preservatives are parabens, such as methyl or propyl p-hydroxybenzoate, and benzalkonium chloride. Examples of humectants are glycerin, propylene glycol, sorbitol, and urea. Examples of other excipients are edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellylose, hydroxypropylcellulose, chitosane, pectin, xanthan gum, carrageenan, locust bean gum, acacia gum, gelatin, and alginates.

Furthermore, pharmaceutically acceptable excipients may comprise substances which inhibit enzymatic degradation and/or alcohols, organic solvents, oils, pH-controlling agents, solubilizers, stabilizers, HLB-controlling agents, viscosity controlling agents, preservatives, osmotic pressure controlling agents, propellants, air displacement, water and mixture thereof. The surfactants may be selected from nonoxynol, octoxynol, tweens, spans, sodium lauryl sulfate, sorbitan monopalmitate; water absorbing polymers may be selected from glycofurols and derivatives thereof; polyethyleneglycol 200-7500 and derivatives thereof, polyvinylpyrrolidone, polyacrylic acid, propyleneglycol, gelatine, cellulose and derivatives thereof, substances which inhibit enzymatic degradation may be selected from aprotinin, DFP, carbopol; oils may be selected from vegetable oil, soybean oil, peanut oil, coconut oil, maize oil, olive oil, sunflower oil, Miglyols; pH-controlling agents may be selected from acetic acid, hydrochloric acid, nitric acid, potassium metaphosphate, potassium phosphate, sodium acetate, ammonia, sodium carbonate, sodium hydroxide, sodium borate, trolamine; solubilizers may be selected from alcohol, isopropyl alcohol, water, glycofurol, polyethyleneglycol 200-7500; stabilizers such as cyclodextrines; HLB controlling agents may be selected from Tween 20-85, Span 20-80, Brij 30-98, acacia; viscosity controlling agents may be selected from cellulose and derivatives thereof, Tweens and derivatives thereof, polyethyleneglycol and derivatives thereof, cetyl alcohol, glycerine, propylene glycol, sorbitol, gelatin; preservatives may be selected from benzalkonium salt, benzyl alcohol, phenol, thimerosal, phenylmercuric nitrate, phenylethyl alcohol, chlorobutanol, cetylpyridinium chloride; osmotic pressure controlling agents may be selected from dextrose, sodium chloride, mannitol; and propellants may be selected from dichlorodifluoromethane, dichlorotetrafluoroethane, trichloromonofluoromethane and other non-ozone damaging propellants such as butane; air displacement may be nitrogen.

The invention will now be exemplified by the following non-limiting examples.

EXAMPLES

Example 1

Formulations with One Stabilizing Additive

Solutions of oxytocin ("99%", Sunbow biotech Ltd.) were prepared as follows: A stock solution (1 mg/mL) was prepared by dissolving oxytocin in 50 mM sodium phosphate buffer pH 4.5. Test solutions were prepared by mixing into water in following order: tetraethyleneglycol (TEG) or other additive, and oxytocin stock solution.

HPLC analysis was performed with Dionex Ultimate 3000, with phosphate buffer (65 mM, pH 5)/acetonitrile. Oxytocin was quantified as AUC, based on standard curve.

Test solutions containing oxytocin (10 ug/mL), and, water, and 2% (vol/vol) of one of (i) raffinose, (ii) tetraethyleneglycol, (iii) methoxypolyethyleneglycol and (iv) polyethyleneglycol 400. The mixed solutions were stored at 40° C. for 32 days. The solutions were analysed with HPLC. Following analysis the tetraethyleneglycol solution showed significantly more stability over other excipients, with about 5% degradation of oxytocin. All other excipients resulted in >22% degradation.

Example 2

Four solutions were prepared containing oxytocin (8 ug/mL) and:
1. 0.4M glucosamine and 6% (v/v) tetraethyleneglycol in water
2. 0.4M glucosamine and 2% (v/v) tetraethyleneglycol in water
3. 0.13M glucosamine and 6% (v/v) tetraethyleneglycol in water
4. 0.13M glucosamine and 2% (v/v) tetraethyleneglycol in water The solutions were stored at 40° C. for 32 days. HPLC analysis showed that mixture 3 resulted in <1% degradation oxytocin; mixture 4 in less 5% degradation, mixtures 1 and 2 in <10%.

However, when these mixtures were autoclaved and challenged with 121° C., mixture 3 and 4 resulted in only 16 and 18% degradation, respectively.

The invention claimed is:

1. A pharmaceutical composition to increase aqueous stability of peptides or proteins, comprising: i) at least one peptide and/or a protein; ii) at least one amino-containing sugar molecule; iii) a polyethyleneglycol, characterized by the presence of less than fourteen ethylene units; and iv) water or isotonic aqueous solution.

2. The composition according to claim 1, wherein the polyethyleneglycol comprises tetraethyleneglycol.

3. The composition according to claim 1, wherein said amino-containing sugar molecule is an amino substituted monosaccharide.

4. The composition according to claim 3, wherein the amino substituted monosaccharide is selected from the group consisting of glucosamine, galactosamine, fructosamine, mannitosamine, and N-acetylglucosamine.

5. The composition according to claim 1, wherein the concentration of the amino-containing sugar is in the range from about 0.001 M to about 1 M concentration.

6. The composition according to claim 1, wherein the concentration of polyethyleneglycol is in the range from about 0.1 to about 10.0% (v/v).

7. The composition according to claim 2, comprising less than 1.0% (v/v) of polyethyleneglycol other than tetraethyleneglycol.

8. The composition according to claim 1, comprising one or more further ingredient selected from sodium chloride, phosphate, and potassium chloride.

9. The composition according to claim 1, which is an isotonic solution.

10. The composition according to claim 1, wherein the peptide or the protein is a therapeutically, prophylactically and/or diagnostically active peptide or protein.

11. The composition according to claim 1 further comprising one or more components selected from the group consisting of surfactants, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, and mixtures thereof.

12. The composition according to claim 1, wherein the peptide or protein is selected from the group consisting of oxytocin and placental protein 13.

13. A method for stabilizing at least one protein or peptide in solution comprising mixing together:
    (i) at least one protein or peptide,
    (ii) tetraethyleneglycol,
    (iii) at least one amino sugar; and
    (iv) water or an aqueous solution.

14. The method according to claim 13, wherein the tetraethyleneglycol is in a concentration from about 0.1 to about 10.0% (v/v).

15. The method according to claim 13, wherein the at least one amino sugar is selected from glucosamine, galactosamine, fructosamine, mannitosamine, and N-acetylglucosamine.

16. The method according to claim 15, wherein the at least one amino sugar is present in a concentration from about 0.001 M to about 1.0 M.

17. The method according to claim 13, wherein the solution is isotonic.

18. The composition according to claim 5, wherein the concentration of the amino-containing sugar is in the range from about 0.05 to about 0.4 M.

19. The composition according to claim 6, wherein the concentration of polyethyleneglycol is in the range from about 0.9 to about 7% (v/v).

20. The composition according to claim 7, comprising less than 0.1% of polyethyleneglycol other than tetraethyleneglycol.

* * * * *